US009884079B2

(12) United States Patent
Chen et al.

(10) Patent No.: US 9,884,079 B2
(45) Date of Patent: Feb. 6, 2018

(54) **BIOLOGICALLY PURE *LACTOBACILLUS MALI* STRAIN AND COMPOSITION THEREOF FOR TREATING METABOLIC SYNDROME**

(71) Applicant: National Taiwan University, Taipei (TW)

(72) Inventors: Ming-Ju Chen, Taipei (TW); Yu-Chun Lin, Taipei (TW); Hsin-Hui Hsieh, Taipei (TW)

(73) Assignee: National Taiwan University, Taipei (TW)

( * ) Notice: Subject to any disclaimer, the term of this patent is extended or adjusted under 35 U.S.C. 154(b) by 50 days.

(21) Appl. No.: 14/976,152

(22) Filed: Dec. 21, 2015

(65) Prior Publication Data

US 2017/0035814 A1 Feb. 9, 2017

(30) Foreign Application Priority Data

Aug. 5, 2015 (TW) .............................. 104125376 A

(51) Int. Cl.
| | |
|---|---|
| *A61K 35/747* | (2015.01) |
| *A61K 45/06* | (2006.01) |
| *A23K 10/18* | (2016.01) |
| *A23L 33/00* | (2016.01) |
| *A23L 33/135* | (2016.01) |
| *C12N 1/20* | (2006.01) |
| *C12R 1/225* | (2006.01) |

(52) U.S. Cl.
CPC ............ *A61K 35/747* (2013.01); *A23K 10/18* (2016.05); *A23L 33/135* (2016.08); *A23L 33/30* (2016.08); *A61K 45/06* (2013.01); *C12N 1/20* (2013.01); *C12R 1/225* (2013.01); *A23V 2002/00* (2013.01); *A23Y 2220/00* (2013.01)

(58) Field of Classification Search
CPC ........ C12N 9/22; C12N 15/63; C12N 15/907; C12N 15/102; C12N 15/1082; C12N 15/86; C12N 15/85; C12N 2750/14143; C12N 15/01; C12N 2800/80; C12N 7/00; C12N 15/11; C12N 15/90; C12N 15/902; C12N 2310/20; C12N 1/20; A23V 2002/00; A23V 2200/3204; A23V 2200/332; A23K 10/18; A23L 33/135; A23L 33/30; A23Y 2220/00; A61K 35/747; A61K 45/06; A61K 2300/00; A61K 31/133; A61K 38/1709; A61K 31/7088; A61K 47/12; A61K 47/26; A61K 2039/53; A61K 39/0011; A61K 45/03; A61K 48/00; A61K 31/661; A61K 39/0007; A61K 9/127
See application file for complete search history.

(56) References Cited

U.S. PATENT DOCUMENTS

| | | | | |
|---|---|---|---|---|
| 2011/0002994 | A1* | 1/2011 | Beaulieu .............. | A61K 38/018 424/484 |
| 2013/0029906 | A1* | 1/2013 | Simard ................ | A61K 38/018 514/6.8 |

OTHER PUBLICATIONS

Stavros Plessas et al., Fermentation 2017, 3, 1, Review pp. 1-10.*
Andersson et al., "Health effects of probiotics and prebiotics, A literature review on human studies," *Scandinavian J. Nutrition*, 45:58-75 (2001).
Bäckhed et al., "Mechanisms underlying the resistance to diet-induced obesity in germ-free mice," *Proc. Nat. Acad. Sci. USA*, 104(3):979-984 (2007).
Bleich et al., "Why Is the Developed World Obese?" National Bureau of Economic Research, working paper 12954, http://www.nber.org/papers/w12954, *Annual Review of Public Health*, vol. 29, 52 pages (2007).
Bloomgarden, "Insulin Resistance: Current Concepts," *Clin. Therap.*, 20(2):216-231 (1998).
Caesar et al., "Effects of gut microbiota on obesity and atherosclerosis via modulation of inflammation and lipid metabolism," *J. Internal Med.*, 268:320-328 (2010).
Cani et al., "Metabolic Endotoxemia Initiates Obesity and Insulin Resistance," *Diabetes*, 56:1761-1772 (2007).
Cani et al., "Selective increases of bifidobacteria in gut microflora improve high-fat-diet-induced diabetes in mice through a mechanism associated with endotoxaemia," *Diabetologia*, 50:2374-2383 (2007).
Cani et al., "Gut microbiota fermentation of prebiotics increases satietogenic and incretin gut peptide production with consequences for appetite sensation and glucose response after a meal," *Am J Clin Nutr.*, 90:1236-1243 (2009).
Cani, "Crosstalk between the gut microbiota and the endocannabinoid system: impact on the gut barrier function and the adipose tissue," *Clin. Microbiol. Infect* ., 18(Suppl. 4):50-53 (2012).
Delzenne and Cani, "Interaction Between Obesity and the Gut Microbiota: Relevance in Nutrition," *Annu. Rev. Nutr.*, 31:15-31 (2011).
Fantuzzi, "Adipose tissue, adipokines, and inflammation," series on Molecular mechanisms in allergy and clinical immunology, *J. Allergy Clin. Immunol.*, 115(5):912-919 (2005).
Frazier et al., "Gut Microbiota, Intestinal Permeability, Obesity-Induced Inflammation, and Liver Injury," J. Parenteral and Enteral Nutrition, 35(Suppl. 1):14S-20S (2011).
Greiner and Bäckhed, "Effects of the gut microbiota on obesity and glucose homeostasis," *Trends in Endocrin. and Metabol.*, 22(4):117-123 (2011).
Hotamisligil, "Inflammation and metabolic disorders," *Nature*, 444:860-867 (2006).
Lye et al., "The Improvement of Hypertension by Probiotics: Effects on Cholesterol, Diabetes, Renin, and Phytoestrogens," *Int. J. Mol. Sci.*, 10:3755-3775 (2009).
Matsuzaki et al., "Antidiabetic Effects of an Oral Administration of *Lactobacillus casei* in Non-Insulin-Dependent Diabetes Mellitus (NIDDM) Model using KK-A$^Y$ Mice," *Endocrine J.*, 44(3):357-365 (1997).

(Continued)

*Primary Examiner* — Debbie K Ware
(74) *Attorney, Agent, or Firm* — McCarter & English, LLP; Yu Lu

(57) ABSTRACT

A *Lactobacillus mali* strain that can be used for treating a metabolic syndrome is provided. A method for treating obesity, diabetes or a complication of diabetes by using the *Lactobacillus mali* strain is also provided.

19 Claims, 11 Drawing Sheets

(56) References Cited

OTHER PUBLICATIONS

McFarland, "A review of the evidence of health claims for biotherapeutic agents," *Microbial Ecology in Health and Disease*, 12:65-76 (2000).

Musso et al., "Gut microbiota as a regulator of energy homeostasis and ectopic fat deposition: mechanisms and implications for metabolic disorders," *Curr. Opin. Lipidol.*, 21:76-83 (2010).

Neyrinck et al., "Dietary modulation of clostridial cluster XIVa gut bacteria (*Roseburia* spp.) by chitin-glucan fiber improves host metabolic alterations induced by high-fat diet in mice," *J. Nutr. Biochem.*, 23:51-59 (2012).

Salminen, "Human studies on probiotics: Aspects of scientific documentation," *Scandinavian J. Nutrition*, 45:8-12 (2001).

Serino et al., "Intestinal microflora and metabolic diseases," *Diabetes & Metabolism*, 35:262-272 (2009).

Sesti, "Pathophysiology of insulin resistance," *Best Practice & Res. Clin. Endocrinol. & Metabol.*, 20(4):665-679 (2006).

Shulman, "Cellular mechanisms of insulin resistance," *J. Clin. Invest.*, 106(2):171-176 (2000).

Tremaroli and Bäckhed, "Functional interactions between the gut microbiota and host metabolism," *Nature*, 489:242-249 (2012).

Yadav et al., "Antidiabetic effect of probiotic dahi containing *Lactobacillus acidophilus* and *Lactobacillus casei* in high fructose fed rats," *Nutrition*, 23:62-68 (2007).

\* cited by examiner

SEQUENCE LISTING

```
<160> NUMBER OF SEQ ID NOS: 4

<210> SEQ ID NO 1
<211> LENGTH: 1498
<212> TYPE: DNA
<213> ORGANISM: Lactobacillus mali
<220> FEATURE:
<221> NAME/KEY: gene
<222> LOCATION: (1)..(1498)
<223> OTHER INFORMATION: 16S rDNA

<400> SEQUENCE: 1
tggctcagga cgaacgctgg cggcgtgcct aatacatgca agtcgaacgc aaaactttca      60
ccgaatgctt gcattcaccg aaagttttga gtggcgaacg ggtgagtaac acgtgggtaa     120
cctgcccaga agagggggat aacacttgga aacaggtgct aataccgcat aacaataaaa     180
accgcatggt ttttatttaa aagatggttt tgctatcact tctggatgga cccgcggcgt     240
attagctagt tggtagggta aaggcttacc aaggcaatga tacgtagccg aactgagagg     300
ttgatcggcc acattgggac tgagacacgg cccaaactcc tacgggaggc agcagtaggg     360
aatcttccac aatggacgaa agtctgatgg agcaacgccg cgtgagtgaa gaaggttttc     420
ggatcgtaaa actctgttgt tagagaagaa cgtgtgtgag agtaactgtt catgcagtga     480
cggtatctaa ccagaaagcc acggctaact acgtgccagc agccgcggta atacgtaggt     540
ggcaagcgtt gtccggattt attgggcgta aagggaacgc aggcggtttt ttaagtctga     600
tgtgaaagcc ttcggcttaa ccgaagtcat gcattggaaa ctgaaagact tgagtgcaga     660
agaggagagt ggaactccat gtgtagcggt gaaatgcgta gatatatgga agaacaccag     720
```

-continued

```
tggcgaaagc ggctctctgg tctgtaactg acgctgaggt tcgaaagtgt gggtagcaaa     780
caggattaga taccctggta gtccacaccg taaacgatga atgctaagtg ttggagggtt     840
tccgcccttc ggtgctgcag ctaacgcatt aagcattccg cctggggagt acgaccgcaa     900
ggttgaaact caaaggaatt gacggggggcc cgcacaagcg gtggagcatg tggtttaatt     960
cgaagcaacg cgaagaacct taccaggtct tgacatcttc tgacagccta agagattagg    1020
tgttcccttc ggggacagaa tgacaggtgg tgcatggttg tcgtcagctc gtgtcgtgag    1080
atgttgggtt aagtcccgca acgagcgcaa cccttattat tagttgccag cattaagttg    1140
ggcactctag tgagactgcc ggtgacaaac cggaggaagg tggggatgac gtcaaatcat    1200 catgccccctt atgacctggg ctacacacgt gctacaatgg acggtacaac gagtcgcgaa    1260
accgcgaggt ttagctaatc tcttaaagcc gttctcagtt cggattgtag gctgcaactc    1320
gcctacatga agtcggaatc gctagtaatc gcggatcagc atgccgcggt gaatacgttc    1380
ccgggccttg tacacaccgc ccgtcacacc atgagagttt gtaacaccca aagccggtga    1440
ggtaaccttt atggggccag ccgtctaagg tgggacagat gattggggtg aagtcgta      1498
```

<210> SEQ ID NO 2
<211> LENGTH: 20
<212> TYPE: DNA
<213> ORGANISM: Artificial
<220> FEATURE:
<223> OTHER INFORMATION: 8f primer
<220> FEATURE:
<221> NAME/KEY: misc_difference
<222> LOCATION: (1)..(20)

<400> SEQUENCE: 2

```
agagtttgat cctggctcag                                                 20
```

<210> SEQ ID NO 3
<211> LENGTH: 18
<212> TYPE: DNA
<213> ORGANISM: Artificial
<220> FEATURE:
<223> OTHER INFORMATION: 1512r primer
<220> FEATURE:
<221> NAME/KEY: misc_difference
<222> LOCATION: (1)..(18)

<400> SEQUENCE: 3

```
aaggaggtga tccagccg                                                   18
```

<210> SEQ ID NO 4
<211> LENGTH: 18
<212> TYPE: DNA
<213> ORGANISM: Artificial
<220> FEATURE:
<223> OTHER INFORMATION: 536f primer
<220> FEATURE:
<221> NAME/KEY: misc_difference
<222> LOCATION: (1)..(18)

<400> SEQUENCE: 4

```
cagcagccgc ggtaatac                                                   18
```

BIOLOGICALLY PURE *LACTOBACILLUS MALI* STRAIN AND COMPOSITION THEREOF FOR TREATING METABOLIC SYNDROME

REFERENCE TO RELATED APPLICATION

This application claims foreign priority under 35 U.S.C. §119(a) to Patent Application No. 104125376, filed on Aug. 5, 2015, in the Intellectual Property Office of Ministry of Economic Affairs, Republic of China (Taiwan, R.O.C.), the entire content of the above-referenced application is incorporated herein by reference.

BACKGROUND OF THE INVENTION

1. Field of the Invention

The present invention is directed to *Lactobacillus mali*, particularly to *Lactobacillus mali* APS1 that is for preventing or treating metabolic syndrome such as obesity, diabetes and complications thereof.

2. Description of Related Art

Due to the changes of habits and customs, obesity becomes the latest epidemic disease (Bleich et al., 2008) and its morbidity is still increasing in the world. According to the estimation from World Health Organization, the obese population will reach 6 million in 2025 (Serino et al., 2009). Obesity is defined as the expanded adipose cells due to excessive accumulation of fat content in body. The weight gain accompanied by abnormal metabolism is mainly contributed by excessive intake of diets which are rich in nutrients. The obese population is a high-risk group of potential complex metabolic syndrome which involves the complex pathological conditions comprising insulin resistance (IR), glucose tolerance change, fatty liver and dyslipidemia, and is associated with various metabolic diseases such as type 2 diabetes and cardiovascular diseases.

According to the statistical results from Ministry of Health and Welfare, Taiwan, diabetes is the fourth cause of top-ten leading causes of death in Taiwan, wherein 95% of diabetes patients belong to non-hereditary type 2 diabetes (Ministry of Health and Welfare, Executive Yuan, 2012). In addition to the high blood glucose level contributed by impaired ability of glucose metabolism, the complications such as retinopathy, nephropathy, and neuropathy and cardiovascular diseases may be developed in a patient suffering from serious diabetes, resulting in greatly increased mortality. However, there is no effective medical treatment for type 2 diabetes. The suggested treatment of type 2 diabetes is still surrounding the control diet and increased amount of exercises.

There are more and more evidences supporting that inflammation plays a critical role in the development of metabolic diseases (Hotamisligil, 2006). Under the condition of long-term nutrition overload, in particular the chronic and low degree inflammation induced by visceral fat, infiltration of macrophages produces a great amount of pro-inflammatory cytokines and chemokines, such as leptin, tumor necrosis factor-α (TNF-α), macrophage chemoattractant protein-1 (MCP-1) and interleukin-6 (IL-6). The function of adipose tissue is changed by these products and the intrinsic adipose cells in adipose tissue of obesity subjects, and the storage of triglyceride and the cycles of free fatty acid are also impaired. Therefore, the pathological disorders in the obesity subject as well as insulin resistance are induced (Fantuzzi, 2005; Sesti, 2006).

Recently, many studies found that intestinal microbiota is significantly relevant to obesity (Backhed et al., 2007). The composition of intestinal microorganisms in healthy subject is very different from that in obese/type 2 diabetes patient, indicating that such composition is an important factor resulting in these metabolic diseases (Cani et al., 2009; Caesar et al., 2010; Musso et al., 2010; Delzenne and Cani, 2011; Frazier et al., 2011; Greiner and Bäckhed, 2011; Cani et al., 2012; Tremaroli and Bäckhed, 2012).

The nutrition source of intestinal microorganisms is mainly from the host's diet, and their interaction can generate energy and stimulate immune system and endocrine (Delzenne and Cani, 2011; Tremaroli and Bäckhed, 2012). In the intestinal microorganisms, the ratio of Gram positive/negative bacteria is closely relevant to the energy metabolism in the host, the endotoxin level in blood and the regulation of inflammation response. Although the mechanism is unclear yet, the interaction of intestinal microorganisms, host gene expression and lifestyle may generate the metabolic symptoms such as obesity and diabetes (Cani et al., 2007 (1); Lye et al., 2009).

Accordingly, probiotics applications gradually emerge in the studies of improving metabolic symptoms. Common probiotics belong to Gram positive bacteria, such as *Lactobacillus* sp. and *Bifidobacterium* sp., which enhance the host health by, for example, inhibiting the growth of pathogen, facilitating the equilibrium of intestinal microbiota, decreasing lactose intolerance and food allergy (McFarland et al., 2000; Anderson et al., 2001; Salminen et al., 2001).

In view of the studies, in Matsuzaki et al. (1997), the insulin-resistance KK-Ay mice were fed with live and dead *Lactobacillus casei*, and found that the blood glucose level and the weights were significantly decreased in eight- to ten-week-old mice. As to the experiment of inducing diabetes symptoms in mice by high-fat diet (HFD), in Cani et al. (2007 (2)), HFD mice fed with the mixed *Bifidobacterium* sp. could improve glucose tolerance and decrease the weight of visceral adipose tissue, in comparing to the control group. In Yadav et al. (2007), mice having hyperglycemia induced by high glucose diet were fed with an India traditional fermentation product containing live *Lactobacillus acidophilus* and *Lactobacillus casei*, and found that mice with this fermented product could significantly reduce the glucose tolerance and the levels of the glucose concentration, total cholesterol, triglyceride, low-density lipoprotein, very low-density lipoprotein and volatile fatty acid in blood, in comparing to the control group. It is thus suggested that the fermentation product containing live *Lactobacillus acidophilus* and *Lactobacillus casei* can reduce the progression of type 2 diabetes induced by obesity.

It can be seen that the ability of probiotics in regulating immunity, decreasing cholesterol level in blood, preventing hypertension, improving eating disorders and alleviating diabetes has been applied in prevention and clinical treatment of metabolic diseases (Lye et al., 2009).

SUMMARY OF THE INVENTION

The present invention found that *Lactobacillus mali* (hereinafter sometimes referred as *Lb. mali*) is capable of improving metabolic syndrome and can be used to prevent or treat metabolic disorder such as obesity and diabetes.

The present invention provides an isolated *Lactobacillus mali* APS1 that has been deposited at DSMZ-DEUTSCHE SAMMLUNG VON MIKROORGANISMEN UND ZELLKULTUREN GmbH (Inhoffenstr. 7B, D-38124 Braunschweig, Germany) on Aug. 6, 2015 and has been given the DSMZ Accession No. DSM 32117 by the International Depositary Authority.

In an aspect of the present invention, a composition is also provided. The composition may include an isolated *Lactobacillus mali* APS1 and a carrier. The isolated *Lactobacillus mali* APS1 is deposited under DSMZ Accession No. DSM 32117.

In one embodiment of the present invention, the composition is a pharmaceutical composition, a dietary supplement or food. In one embodiment of the present invention, the composition is an oral formulation. Preferably, the oral formulation is in a form selected from the group consisting of solution, suspension, emulsion, powder, tablet, pill, syrup, lozenge, troche, chewing gum, capsule and a combination thereof.

In one embodiment of the present invention, the composition may further include a bacterial strain selected from the group consisting of *Lactobacillus* sp., *Bifidobacterium* sp., *Streptococcus* sp., yeast, *Enterococcus* sp., *Bacillus* sp. and a combination thereof.

In one embodiment of the present invention, the carrier included in the composition is an edible material selected from the group consisting of water, milk, whey, fermented milk, yogurt, powdered milk, cheese, fruit juice, vegetable juice, soy milk, bean milk, fermented soy milk, sport drink, dessert, candy, Chinese herbal medicine, animal feed, corn starch, wheat starch, cassava starch, maltodextrin and a combination thereof.

In another aspect of the present invention, a method for preventing or treating a metabolic syndrome in a subject is provided. In one embodiment of the present invention, the *Lactobacillus mali* is the isolated *Lactobacillus mali* APS1 that is deposited under DSMZ Accession No. DSM 32117.

In one embodiment of the present invention, the metabolic syndrome is selected from the group consisting of obesity, diabetes, a complication of diabetes, hyperlipidemias, hyperglycemia, fatty liver, hyperuricemia, hypertension and a combination thereof.

In one embodiment of the present invention, the metabolic syndrome is obesity. In one embodiment of the present invention, after administrating the *Lactobacillus mali*, a body weight of the subject is reduced and/or a weight gain in the subject is inhibited. In an embodiment, the obesity is resulted from body fat formation or increased content of visceral fat.

In another embodiment of the present invention, the metabolic syndrome is diabetes or a complication of diabetes. In one embodiment of the present invention, the diabetes is resulted from a factor selected from the group consisting of insulin resistance, impaired glucose tolerance, hyperglycemia, hypertriglyceridemia, high total cholesterol, high ratio of LDL/HDL, low concentration of GLP-1 and a combination thereof. In an embodiment, the diabetes is type 2 diabetes, and the complication of diabetes is selected from the group consisting of retinopathy, nephropathy, neuropathy, cardiovascular disease and a combination thereof.

In one embodiment of the present invention, after administrating the *Lactobacillus mali*, an amount of one selected from the group consisting of glucose, total cholesterol and a combination thereof in the subject is reduced. In another embodiment of the present invention, after administrating the *Lactobacillus mali*, an amount of incretin in the subject is increased. Preferably, the incretin is GLP-1.

BRIEF DESCRIPTION OF THE DRAWINGS

FIGS. 2A(a) and 2A(b) show the weekly body weight variations and the weight gain trends after the 8 weeks of experimental treatments.

FIGS. 3A and 3B show the changes of blood glucose in an oral glucose tolerance test and the area under curve of blood glucose ($AUG_{glucose}$) at the $4^{th}$ week, respectively; FIGS. 3C and 3D show the changes of blood glucose in an oral glucose tolerance test and the area under curve of blood glucose ($AUG_{glucose}$) at the $8^{th}$ week, respectively; FIGS. 3E to 3G show the levels of glucose, GLP-1 and insulin in blood, respectively; FIG. 3H shows the homeostatic model assessment-insulin resistance (HOMA-IR) index. CT: control group, fed with normal control diet containing 10% fat; HFD: high-fat diet group, fed with high-fat diet containing 60% fat; HFD+M1: M1 group, fed with high-fat diet and $10^8$ CFU of *Lb. kefiranofaciens* M1; HFD+APS1: APS1 group, fed with high-fat diet and $10^8$ CFU of *Lb. mali* APS1. Data is represented by the means SD. *$P<0.05$, $P<0.01$, *$P<0.001$. The P value is compared with the control group unless the drawings clearly indicate otherwise.

FIG. 4A shows the weekly mean average of food intake of the mice; FIG. 4B shows the body weight loss in mice after feeding with or without *Lb. mali* APS1 for 4 weeks; FIGS. 4C and 4D show the weight of body fat and the weight of liver after feeding with or without *Lb. mali* APS1 for 4 weeks, respectively. Normal mice: fed with normal control diet containing 10% fat; Obese mice: fed with high-fat diet for 8 weeks followed by normal control diet for 4 weeks; Obese mice+APS1: probiotics-treated group, fed with high-fat diet for 8 weeks followed by normal control diet and $10^8$ CFU of *Lb. mali* APS1 for 4 weeks. Data is represented by the means SD. *$P<0.05$. The P value is compared with the control group unless the drawings clearly indicate otherwise.

DETAILED DESCRIPTION OF THE PREFERRED EMBODIMENTS

Figure 1:
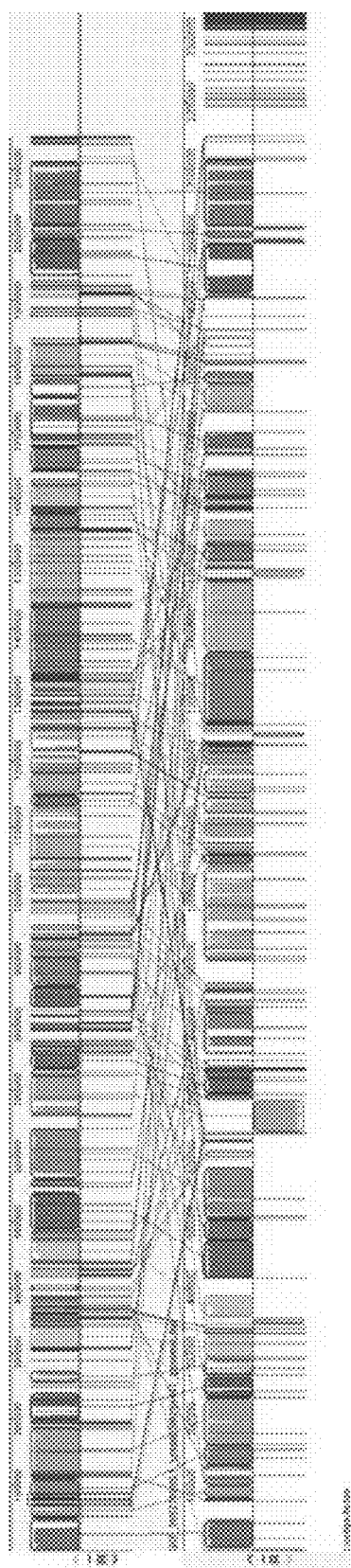
FIG. 1 shows the difference between the genomic DNA sequences of *Lb. mali* APS1 (upper panel) and *Lb. mali* KCTC 3596 (lower panel).

The following specific examples are used for illustrating the present invention. A person skilled in the art can easily conceive the other advantages and effects of the present invention. The present invention can also be implemented by different specific cases be enacted or application, the details of the instructions can also be based on different perspectives and applications in various modifications and changes do not depart from the spirit of the present invention.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The present invention is directed to a use of *Lactobacillus mali* for preventing or treating metabolic syndrome such as obesity, diabetes, and complications thereof.

The term "insulin resistance" used herein refers to a pathological condition in which the insulin sensitivity of target tissues is decreased. Insulin resistance may result in decreased glucose transport and reduced glycogenesis. Insulin resistance may be directly induced under chronic hyperglycemic condition resulting from the intake of excessive concentration of nutrients. The mechanism of insulin resistance involves the reduced number of receptors in the cells and the decreased insulin affinity, resulting in the change of cell membrane's characteristics. Thereby, the insulin receptors cannot be phosphorylated easily, and then the signal transduction of blood glucose balance by the insulin receptors is affected. These defects will be reflected in disturbance of glucose metabolism of the target tissues (Bloomgarden, 1998). Insulin resistance associated with obesity is a key factor in type 2 diabetes progression. The blood glucose level in the obese cannot return to normal level because the glucose metabolism in target tissues is decreased. Therefore, the long-term hyperglycemia may result in apoptosis of pancreatic β-cells and dysfunction, and the increased level of free fatty acid in the body may inhibit the oxidation, absorption and utilization of glucose in muscle. It leads to the disturbance of the mechanism of blood glucose reduction in the subject, and then insulin resistance is induced. In addition, insulin resistance may also induce the development of hypertension, dyslipidemia, atherosclerosis and cardiovascular diseases, indicating that insulin resistance is a common symptom in many clinical diseases, including metabolic syndrome, i.e., a collection of conditions comprising impaired glucose tolerance, obesity, dyslipidemia and hypertension (Sesti, 2006).

The term "glucagon-like peptide-1 (GLP-1)" used herein refers to a kind of incretin hormone, which is secreted by the intestinal L cells after food stimulation. GLP-1 has the insulinotropic ability to promote insulin synthesis and production from pancreatic β-cells, so as to facilitate blood glucose metabolism and maintain homeostasis.

The term "metabolic syndrome" used herein comprises obesity, diabetes, hyperlipidemias (e.g., hypertriglyceridemia and hypercholesteremia), hyperglycemia, fatty liver, cardiovascular disease, hyperuricemia, hypertension associated with insulin resistance, and so on.

The phrase "oral glucose tolerance test" used herein refers to diagnostic criteria for diabetes recommended by World Health Organization, which can be used to detect the incubation period of type 2 diabetes (Shulman, 2000). After a subject with normal or slightly higher blood glucose level took the oral glucose tolerance test, the abnormally increased level of insulin, if any, can be considered as evidences that the insulin sensitivity is decreased and pancreatic β-cells is dysfunctional.

The term "treating/treatment" used herein does not necessarily mean curing a disease or disorder. A reduction in symptoms associated with the disorder or disease can also be characterized as a treatment. Further, an alleviation in the progression of the disorder or disease can also be characterized as a treatment.

The term "effective amount" used herein refers to the amount of a substance required to achieve the particular utility. Thus, an effective amount can vary depending upon a particular use. The effective amount of *Lactobacillus mali* used in the present invention may be determined by many factors, including the type of the disease to be treated, administration routes, ages of the patients, genders of the patients, weights of the patients, and disease severity.

In addition, the composition comprising *Lactobacillus mali* used in the present invention may further comprise a pharmaceutically acceptable carrier. For an oral formulation, the pharmaceutically acceptable carrier may comprise binding agent, lubricant, decomposer, excipient, solubilizing agent, dispersing agent, stabilizing agent, suspending agent, coloring agent and flavoring agent. The examples of the pharmaceutically acceptable carriers include lactose, glucose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinylpyrrolidone, water, methylhydroxybenzoate, propylhydroxy-benzoate, talc, magnesium stearate and mineral oils.

Many examples have been used to illustrate the present invention. The examples below should not be taken as a limit to the scope of the invention.

EXAMPLE

Example 1: 16s rDNA Sequence Identification

*Lactobacillus mali* (*Lb. mali*) APS1 was isolated from fermented food by Animal Production Laboratory of National Taiwan University. The process of culturing such bacterial strain was as follows. 5% (w/w) of sugary kefir grain was seeded in a mixture of 5% (w/v) of black sugar solution (formulated by black sugar powder), whole milk and whole goat milk which had been autoclaved at 121° C. for 15 minutes, followed by subjected to fermentation in constant temperature incubator at 20° C. Subsequently, 10 g of the activated sugary kefir grain was washed with sterilized water and placed in a sterile sample bag. Ninety g of the autoclaved sodium chloride solution (0.85%) was added into the sterile sample bag. After homogenization at normal speed for 2 min by sample mixer, 1 mL the homogenate was subjected to serial dilution and culture.

The process of isolating single colonies of microorganisms was as follows. All single colonies on a culture medium having 30 to 100 colonies obtained from the above process were picked out and placed in a suitable culture liquid medium for activation. After then, the culture liquid medium was aliquot into 1.5 mL microcentrifuge tubes for the future use of stain identification.

The full length of gene fragment of 16S rDNA of the lactic acid bacterium was amplified by universal primers 8f and 1512r. The obtained products were subject to sequencing analysis by using primers 8f, 536f and 1512r (see Table 1) for three-stage full sequencing. The sequencing result showed that the sequence of 16s rDNA of the isolated *Lb. mali* was represented by the sequence below:

```
                                               (SEQ ID NO: 1)
TGGCTCAGGA CGAACGCTGG CGGCGTGCCT AATACATGCA

AGTCGAACGC AAAACTTTCA CCGAATGCTT GCATTCACCG

AAAGTTTTGA GTGGCGAACG GGTGAGTAAC ACGTGGGTAA

CCTGCCCAGA AGAGGGGGAT AACACTTGGA AACAGGTGCT
```

-continued

AATACCGCAT AACAATAAAA ACCGCATGGT TTTTATTTAA

AAGATGGTTT TGCTATCACT TCTGGATGGA CCCGCGGCGT

ATTAGCTAGT TGGTAGGGTA AAGGCTTACC AAGGCAATGA

TACGTAGCCG AACTGAGAGG TTGATCGGCC ACATTGGGAC

TGAGACACGG CCCAAACTCC TACGGGAGGC AGCAGTAGGG

AATCTTCCAC AATGGACGAA AGTCTGATGG AGCAACGCCG

CGTGAGTGAA GAAGGTTTTC GGATCGTAAA ACTCTGTTGT

TAGAGAAGAA CGTGTGTGAG AGTAACTGTT CATGCAGTGA

CGGTATCTAA CCAGAAAGCC ACGGCTAACT ACGTGCCAGC

AGCCGCGGTA ATACGTAGGT GGCAAGCGTT GTCCGGATTT

ATTGGGCGTA AAGGGAACGC AGGCGGTTTT TTAAGTCTGA

TGTGAAAGCC TTCGGCTTAA CCGAAGTCAT GCATTGGAAA

CTGAAAGACT TGAGTGCAGA AGAGGAGAGT GGAACTCCAT

GTGTAGCGGT GAAATGCGTA GATATATGGA AGAACACCAG

TGGCGAAAGC GGCTCTCTGG TCTGTAACTG ACGCTGAGGT

TCGAAAGTGT GGGTAGCAAA CAGGATTAGA TACCCTGGTA

GTCCACACCG TAAACGATGA ATGCTAAGTG TTGGAGGGTT

TCCGCCCTTC GGTGCTGCAG CTAACGCATT AAGCATTCCG

CCTGGGGAGT ACGACCGCAA GGTTGAAACT CAAAGGAATT

GACGGGGGCC CGCACAAGCG GTGGAGCATG TGGTTTAATT

CGAAGCAACG CGAAGAACCT TACCAGGTCT TGACATCTTC

TGACAGCCTA AGAGATTAGG TGTTCCCTTC GGGGACAGAA

TGACAGGTGG TGCATGGTTG TCGTCAGCTC GTGTCGTGAG

ATGTTGGGTT AAGTCCCGCA ACGAGCGCAA CCCTTATTAT

TAGTTGCCAG CATTAAGTTG GGCACTCTAG TGAGACTGCC

GGTGACAAAC CGGAGGAAGG TGGGGATGAC GTCAAATCAT

CATGCCCCTT ATGACCTGGG CTACACACGT GCTACAATGG

ACGGTACAAC GAGTCGCGAA ACCGCGAGGT TTAGCTAATC

TCTTAAAGCC GTTCTCAGTT CGGATTGTAG GCTGCAACTC

GCCTACATGA AGTCGGAATC GCTAGTAATC GCGGATCAGC

ATGCCGCGGT GAATACGTTC CCGGGCCTTG TACACACCGC

CCGTCACACC ATGAGAGTTT GTAACACCCA AAGCCGGTGA

GGTAACCTTT ATGGGGCCAG CCGTCTAAGG TGGGACAGAT

GATTGGGGTG AAGTCGTA

The sequencing result was used to identify the bacterial strain by Basic Local Alignment Search Tool (BLAST) in Genbank. The result of sequence alignment was reported in Table 2.

TABLE 1

Primer sequences

| Primer | Sequence |
|---|---|
| 8f | 5'-AGA GTT TGA TCC TGG CTC AG-3' (SEQ ID NO: 2) |
| 1512r | 5'-AAG GAG GTG ATC CAG CCG-3' (SEQ ID NO: 3) |
| 536f | 5'-CAG CAG CCG CGG TAA TAC 3' (SEQ ID NO: 4) |

TABLE 2 result of sequence alignment for 16S rDNA

| Bacterial strain | Identity (%) |
|---|---|
| Lb. mali LA214 (FM878596.1) | 100 |
| Lb. mali JCM 8611 (AB690199.1) | 99 |
| Lb. mali JCM 8612 (AB690200.1) | 99 |
| Lb. mali NBRC 102159 (NR 112691.1) | 99 |
| Lb. mali KS6 (FJ157230.1) | 99 |

The sequence of the isolated Lb. mali APS1 was further compared with that of Lb. mali LA214. It was found that the full-length 16s rDNA sequence of Lb. mali APS1 had 1498 nucleotides, while that of Lb. mali LA214 had only 1429 nucleotides (corresponding to the $38^{th}$ to $1466^{th}$ nucleotides in 16s rDNA of Lb. mali APS1). It was confirmed that the isolated Lb. mali APS1 of the present invention was a novel Lb. mali strain.

After bacterial strain identification, Lb. mali APS1 was then deposited under Budapest Treaty at Leibniz Institute DSMZ-German Collection of Microorganisms and Cell Cultures (Inhoffenstr. 7 B, D-38124 Braunschweig, Germany) on Aug. 6, 2015 and was given the DSMZ Accession No. DSM 32117 by the International Depositary Authority. This biological material was subjected to the viability test and passed.

Example 2: Chromosome Sequencing and Alignment

Genomic DNA of Lb. mali APS1 was extracted by PRESTO™ Mini gDNA Bacteria Kit (Geneaid Biotech. Ltd.) according to the manufacturer's instructions. The extracted DNA samples with OD 260/280 (OD, optical density) in the range of 1.8 to 2.0 and quantity ratio over 0.7 measured by Qubit versus NanoDrop was acceptable for further processing of chromosome sequencing.

Then, 10 μg of total DNA was sonicated by Misonix 3000 sonicator to the sizes ranging from 400 to 500 bp. DNA sizing was checked by bioanalyzer DNA 1000 chip (Agilent Technologies). For constructing the sequence library, 1 μg of the sonicated DNA was end-repaired, A-tailed and adaptor-ligated followed by the Illumina's TruSeq DNA preparation protocol.

The DNA sequences generated were subject to a filtering process to obtain the qualified reads. Trimmomatic was implemented to trim or remove the reads according to the quality score. Cleaned and filtered nuclear reads were assembled de novo using Velvet. Genome annotations were created in MAKER 2.00 using a GeneMark model trained for *Lb. mali* via self-training. The resulting predictions were searched against NCBI non-redundant (nr) database by using BLASTP.

FIG. 1 was the alignment result of *Lb. mali* APS1 and the known bacterial strain (*Lb. mali* KCTC 3596=DSM 20444), showing the similarity and difference between the genomic DNA sequences of *Lb. mali* APS1 and *Lb. mali* KCTC 3596. As shown in FIG. 1, upper panel illustrated the genomic DNA sequences of *Lb. mali* APS1, and lower panel illustrated the genomic DNA sequences of *Lb. mali* KCTC 3596. The alignment result showed that the similarity between the genomic DNA sequences of *Lb. mali* APS1 and *Lb. mali* KCTC 3596 was 54.54%.

Example 3: Carbon Source Utilization for *Lb. Mali* APS1

The utilization of carbon source from various carbohydrate substrates for *Lb. mali* APS1 was determined by Analytical Profile Index (API), and the results were shown in Table 3.

TABLE 3

Results of Carbon Source Utilization for *Lb. mali* APS1 by API

| Carbohydrates Substrate Strips | *Lb. mali* APS1 |
|---|---|
| D-Ribose | − |
| D-Xylose | − |
| D-Galactose | − |
| D-Glucose | + |
| D-Fructose | + |
| D-Mannose | + |
| L-Sorbose | + |
| D-Mannitol | − |
| D-Sorbitol | − |
| Methyl-α-D-mannopyranoside | − |
| Methyl-α-D-glucopyranoside | − |
| N-Acetyl glucosamine | + |
| Amygdalin | + |
| Arbutin | − |
| Esculin ferric citrate | + |
| Salicin | + |
| D-Cellobiose | + |
| D-Maltose | + |
| D-Lactose | − |
| D-Melibiose | − |
| Sucrose | + |
| D-Trehalose | + |
| Amygdalose | + |
| D-Turanose | − |
| D-Tagatose | − |
| Potassium gluconate | − |

+: positive;
−: negative

Example 4: Lactic Acid Bacteria Sample Preparation 1 mL of liquid containing *Lb. mali* APS1 was serially diluted and then cultured in Lactobacilli deMan, Rogosa and Sharp (MRS) medium (Lactobacilli MRS agar, Merck) for 48 hrs at 37° C. Subsequently, a culture medium group having 30 to 300 colonies was selected, and then single colonies on the surface of the medium were picked out and placed in MRS liquid medium for activation. After then, the MRS medium was aliquot into 1.5 mL microcentrifuge tubes, and stored for future testing. The cryogenic vial containing *Lb. mali* APS1 was activated by MRS medium (Difco Laboratories, Detroit, Mich.) at 37° C. Further, the bacteria in logarithmic phase were harvested by centrifugation, and then resuspended in phosphate buffer solution (PBS) (Hyclone, South Logan, Utah) to a final concentration of $10^8$ colony formation unit (CFU)/mL.

Example 5: Obesity Animal Model Establishment

Forty seven-week-old female C57BL/6jNarl (BioLASCO Taiwan Co., Ltd, Taipei, Taiwan) were independently housed in cages with bedding (Beta Chip® heat treated hardwood laboratory bedding, Northeastern Products Corp., Warrensburg, N.Y., USA) and fed with chow diet and water ad libitum at Laboratory Animal Center under a temperature of 22° C. to 25° C., 40% to 60% humidity and 12-h light/dark cycle, and equipping ventilating fan for approximately one week.

Then, the mice were fed with high-fat diet for obesity induction according to Neyrinck et al. (2012). The mice were divided into 4 groups (10 per group): (1) control group (CT) fed with normal control diet containing 10% fat (D12450B; research diets, Inc., New Brunswick, N.J., USA); (2) high-fat diet group (HFD) fed with high-fat diet containing 60% fat and orally administrated with PBS daily; and two probiotics groups: (3) M1 group (HFD+M1) and (4) *Lb. mali* APS1 group (HFD+APS1), fed with high-fat diet, and orally administrated with $10^8$ CFU of *Lb. kefiranofaciens* M1 and $10^8$ CFU of *Lb. mali* APS1 daily for 8 weeks, respectively. Their weight and food intake were observed and recorded every week.

High-fat diet included 60% fat, 20% carbohydrate and 20% protein [kcal/100 g] (D12492; Research Diets, Inc., New Brunswick, N.J., USA). The food intake for high-fat diet was lower than that for normal diet. The high-fat diet can result in weight gain in mice in short period of time, such that the feed process of animal for metabolism experiment can be effectively shortened. By refined ingredients, the dilution of other nutrients due to high-fat content can be reduced.

Example 6: Effects of *Lb. Mali* APS1 on Weight Gain Due to High-Fat Diet

Figure 2A:
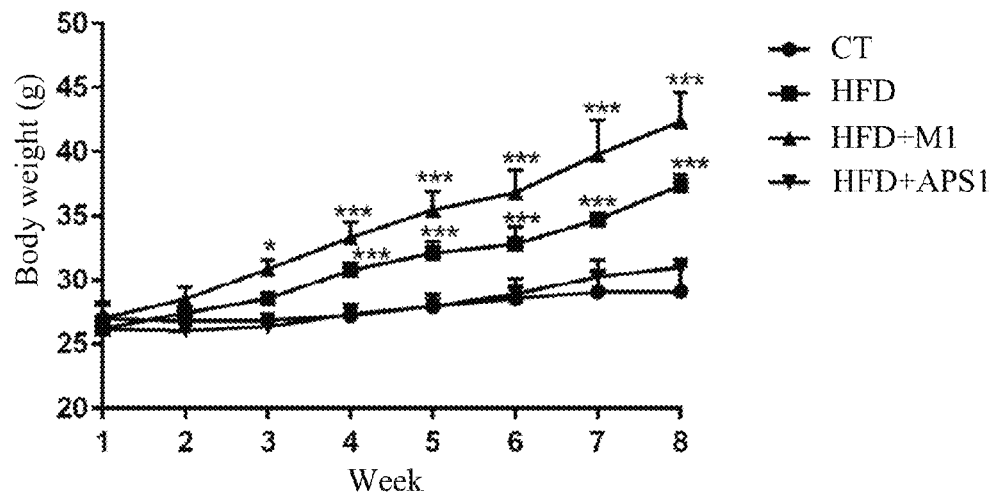
FIGS. 2A(a) to 2E show the effect of *Lb. mali* APS1 on body weight gain induced by high-fat diet in mice.
Figure 2A:
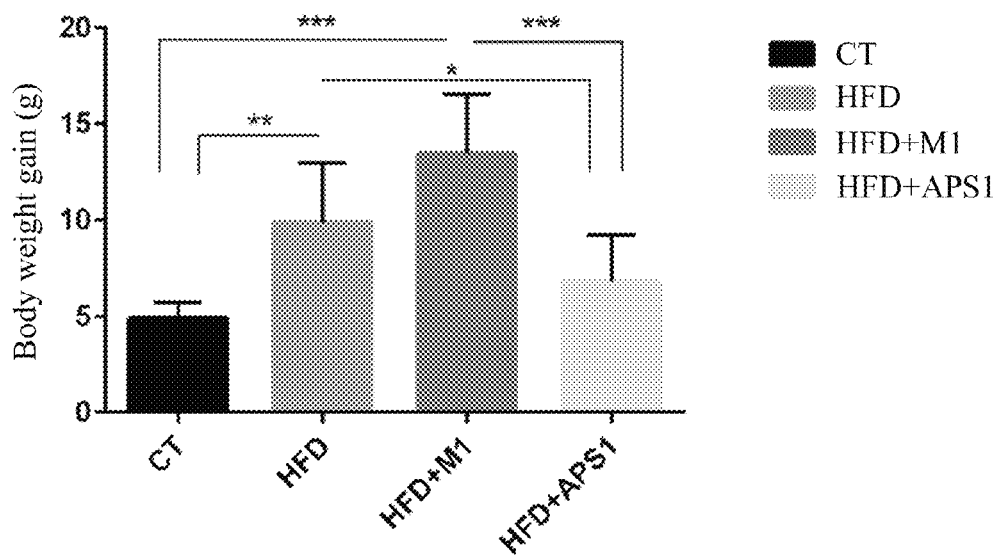

As shown in FIGS. 2A(a) and 2A(b), the mice fed with high-fat diet for 8 weeks had continually gained 10 to 15% body weight per week, and the group fed with *Lb. mali* APS1 exhibited a significant effect on relieving weight gain.

Figure 2B:
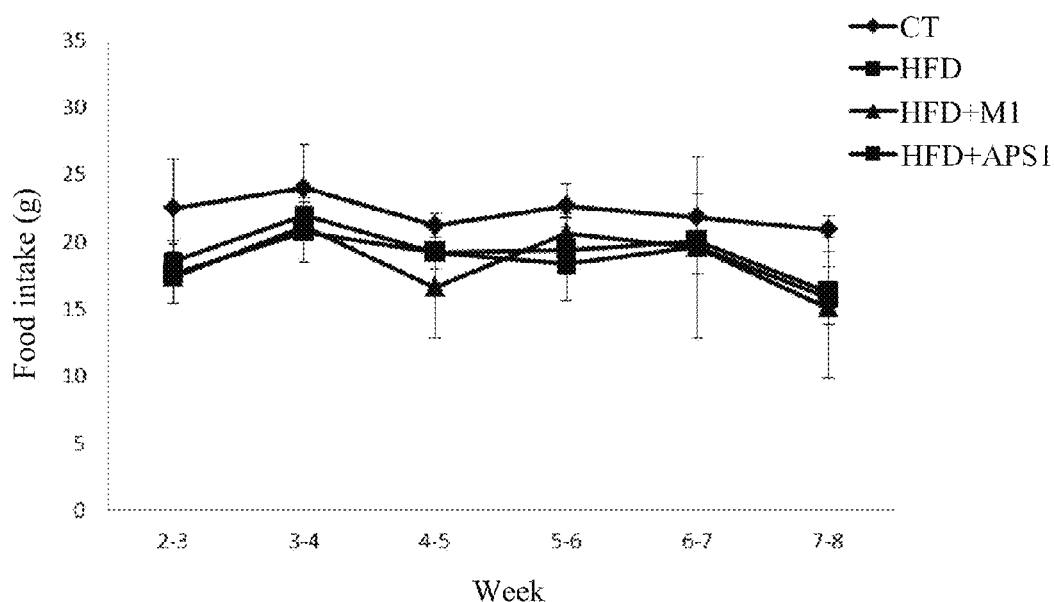
FIGS. 2B(a) and 2B(b) show the changes in weekly food intake and the total food intake in 8 weeks.
Figure 2B:
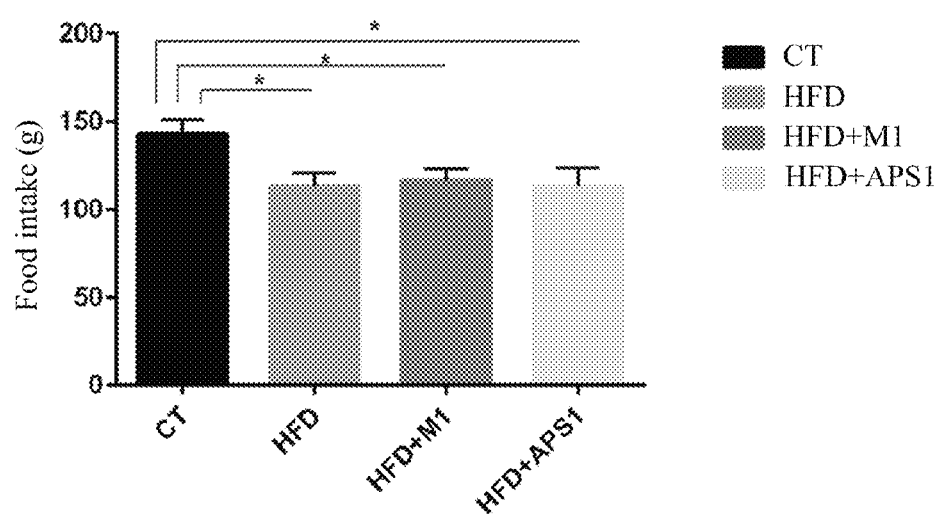

In view of the significant changes in weight difference, the food intake was also determined in this example. As shown in FIGS. 2B(a) and 2B(b), it was found that there was no significant difference in the weekly food intakes among the three groups fed with high-fat diet (HFD group, M1 group and APS1 group). It indicated that the weight differences of the mice did not result from the food intake difference.

Example 7: Body Composition Analysis

To confirm whether the weight difference resulted from the change of body composition, the mice which had been fed in the same manner as Example 5 were subject to body composition analysis by Minispec LF50 TD-NMR (Time-Domain Nuclear Magnetic Resonance analyzer, Bruker Madison, USA) to analyze the body composition including body fat, body lean and body fluid. Further, SkyScan1176 Micro-CT System (Micro Photonics Inc., Allentown, Pa., USA) was used to perform micro-computed tomography for in vivo imaging and analyzing the accumulation profile of body fat in the mice.

Figure 2C:
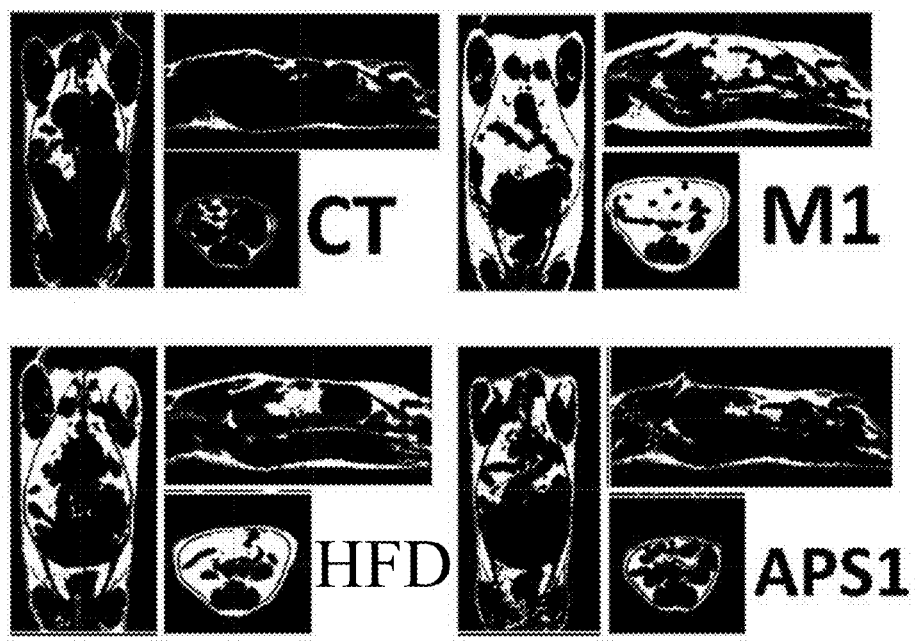
FIG. 2C are representative Micro-CT scanning images of mouse body fat accumulation after 8 weeks.
Figure 2D:
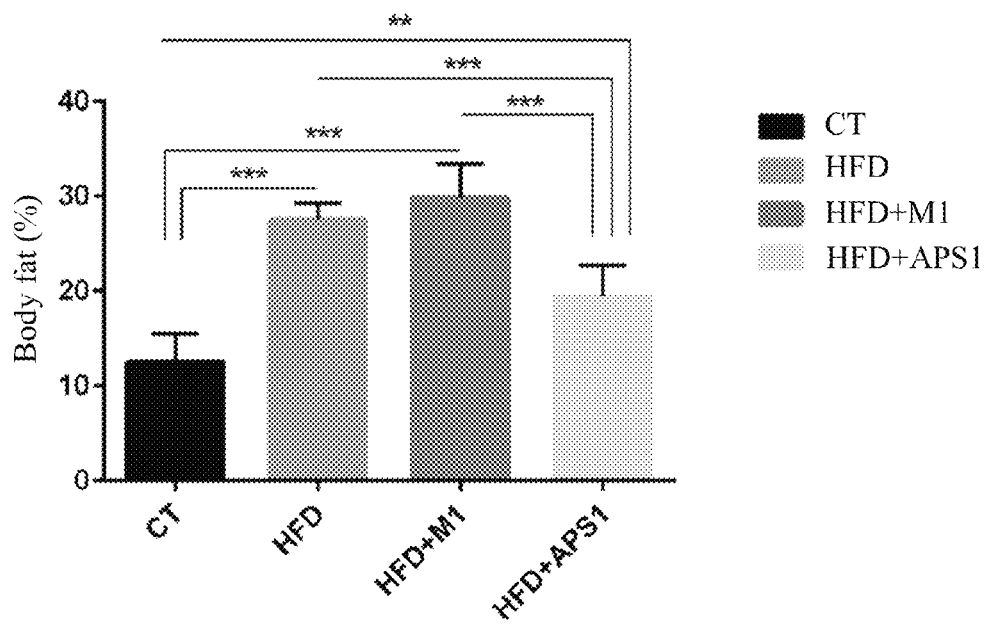
FIG. 2D shows the ratio of body fat and body lean in whole body measured by TD-NMR.
Figure 2E:
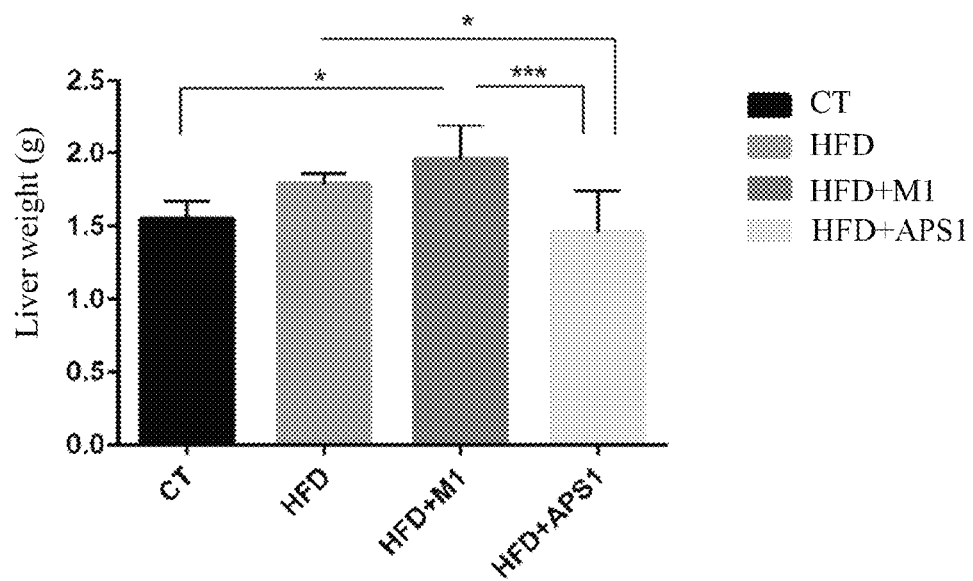
FIG. 2E shows the weight of liver. CT: control group, fed with normal control diet containing 10% fat; HFD: high-fat diet group, fed with high-fat diet containing 60% fat; HFD+M1: M1 group, fed with high-fat diet and $10^8$ CFU of *Lb. kefiranofaciens* M1; HFD+APS1: APS1 group, fed with high-fat diet and $10^8$ CFU of *Lb. mali* APS1. Data is represented by the means SD. *$P<0.05$, $P<0.01$, *$P<0.001$. The P value is compared with the control group unless the drawings clearly indicate otherwise.

As shown in FIGS. 2C and 2D, Lb. mali APS1 significantly reduced the body fat accumulation in the mice, and the ratio of body fat in whole body in APS1 group was 19.4±3.24%, which was much lower than that in HFD group (27.15±1.7%). FIG. 2E shows the liver weight. It was found that the significant weight gain in liver due to fat accumulation resulting from high-fat diet could be avoided by feeding Lb. mali APS1, and there was no significant difference between the liver weight of APS1 group and that of control group fed with normal diet.

Example 8: Plasma Biochemical Parameter Analysis

Since the insulin resistance patients usually have the symptoms such as hyperglycemia, hyperinsulinemia and hyperlipidemias, the measurements of the levels of glucose, serum insulin, triglyceride, cholesterol and free fatty acid in blood become important indicators for screening a bacterial strain which can reduce insulin resistance.

This analysis was performed by blood biochemical analyzer (FDC 3500, Fujifilm, Tokyo, Japan) to determine the levels of fasting blood glucose (GLU), triglyceride (TG), total cholesterol (T-CHOL), high-density lipoprotein cholesterol (HDL-cholesterol) and low-density lipoprotein cholesterol (LDL-cholesterol), and blood urea nitrogen (BUN) in the mice which were fed in the same manner as Example 5 for 8 weeks.

The results were reported in Table 4. It was found that the levels of GLU and T-CHOL in the mice were significantly reduced by feeding Lb. mali APS1.

TABLE 4

Plasma biochemical parameters in mice

| Parameters (mg/dL) | CT group | HFD group | M1 group | APS1 group |
| --- | --- | --- | --- | --- |
| GLU | 147.50 ± 14.60 | 192.88 ± 07.12 | 201.83 ± 19.42 | 175.78 ± 07.36 |
| BUN | 24.12 ± 03.72 | 24.28 ± 03.58 | 23.60 ± 02.10 | 23.65 ± 03.76 |
| T-CHO | 136.24 ± 12.08 | 158.83 ± 10.70* | 171.90 ± 22.82* | 148.52 ± 21.29 |
| TG | 57.20 ± 34.90 | 78.65 ± 31.78 | 75.83 ± 13.06 | 60.60 ± 17.76 |
| Calcium | 7.28 ± 00.44 | 7.53 ± 00.79 | 8.45 ± 00.78 | 7.66 ± 00.69 |
| HDL | 125.56 ± 09.57* | 146.08 ± 10.20* | 157.08 ± 23.18# | 136.28 ± 17.43* |
| LDL | 19.20 ± 05.64 | 19.50 ± 03.58 | 20.95 ± 05.88 | 13.47 ± 04.75* |

CT group: fed with normal control diet containing 10% fat;
HFD group: fed with high-fat diet containing 60% fat;
M1 group: fed with high-fat diet and $10^8$ CFU of Lb. kefiranofaciens M1;
APS1 group: fed with high-fat diet and $10^8$ CFU of Lb. mali APS1.
Data is represented by the means SD.
*P <0.01, compared with CT group;
P < 0.05, compared with HFD group.

Example 9: Oral Glucose Tolerance Test (OGTT)

For determining the blood glucose change in mice, the obesity animal model was established in the same manner as Example 5, and the oral glucose tolerance test was performed at the $4^{th}$ week and the $8^{th}$ week. The mice were fasted for 6 hrs before the test and followed by orally administrating with glucose (3 g/kg-weight, 66% glucose solution). The tail vein blood sampling was performed at 30 min prior to glucose administration, just after glucose administration, and at 15 min, 30 min, 60 min, 90 min and 120 min after glucose administration. Also, the blood glucose level was determined by blood glucose meter (Roche Diagnostics, Indiana, USA). The area under curve of glucose ($AUG_{glucose}$) in blood was then calculated.

Figure 3A:
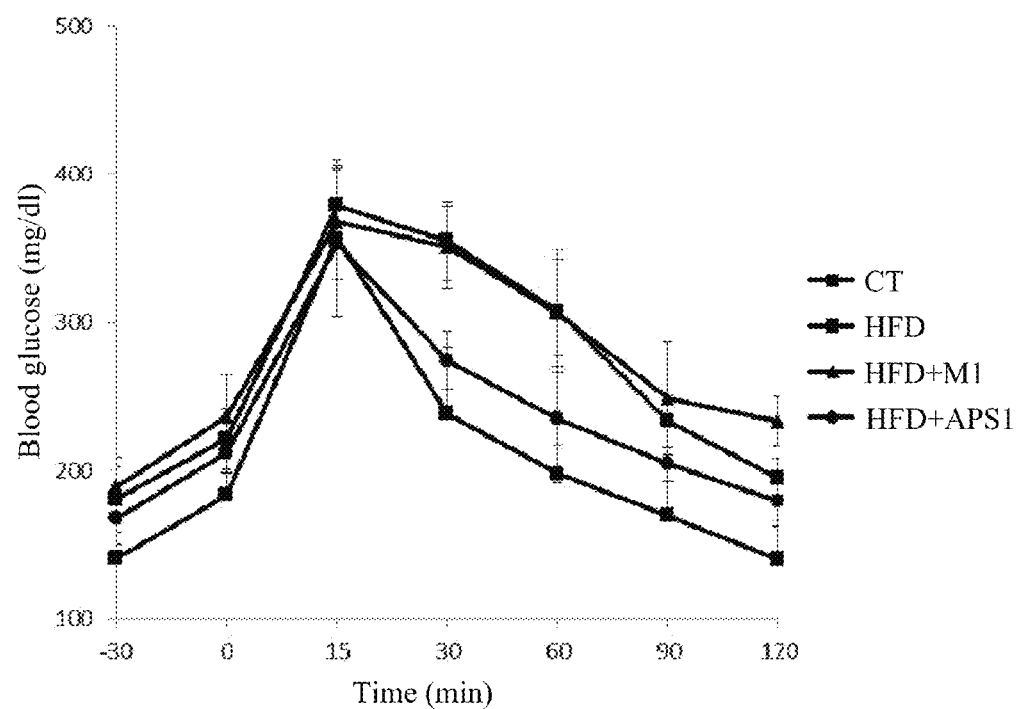
FIGS. 3A to 3H show the effect of *Lb. mali* APS1 on glucose tolerance, metabolic hormones and insulin resistance in mice fed with high-fat diet.
Figure 3B:
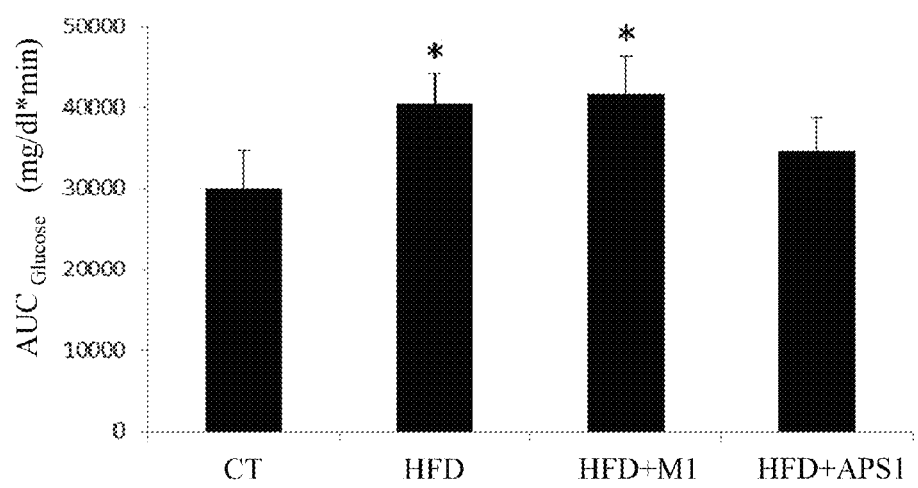
Figure 3C:
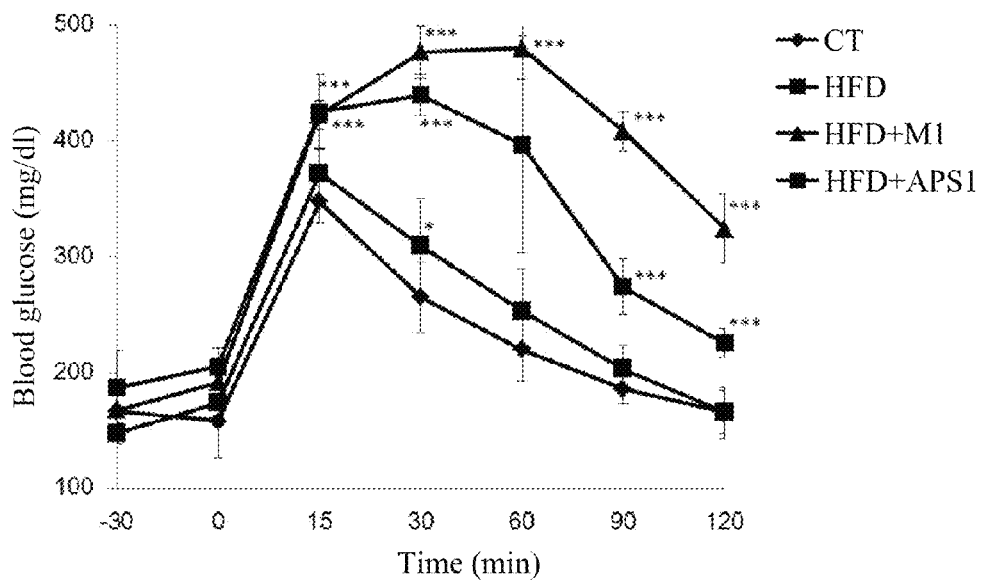
Figure 3D:
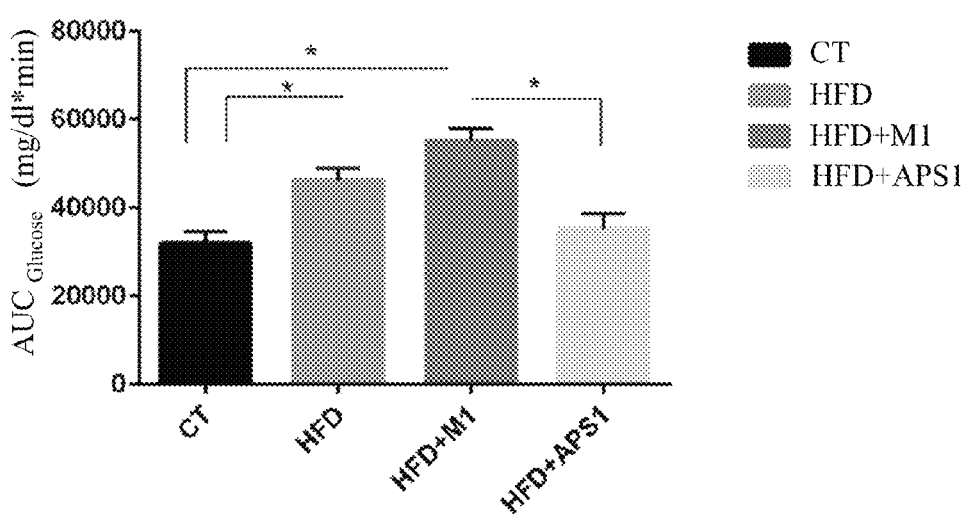
Figure 3E:
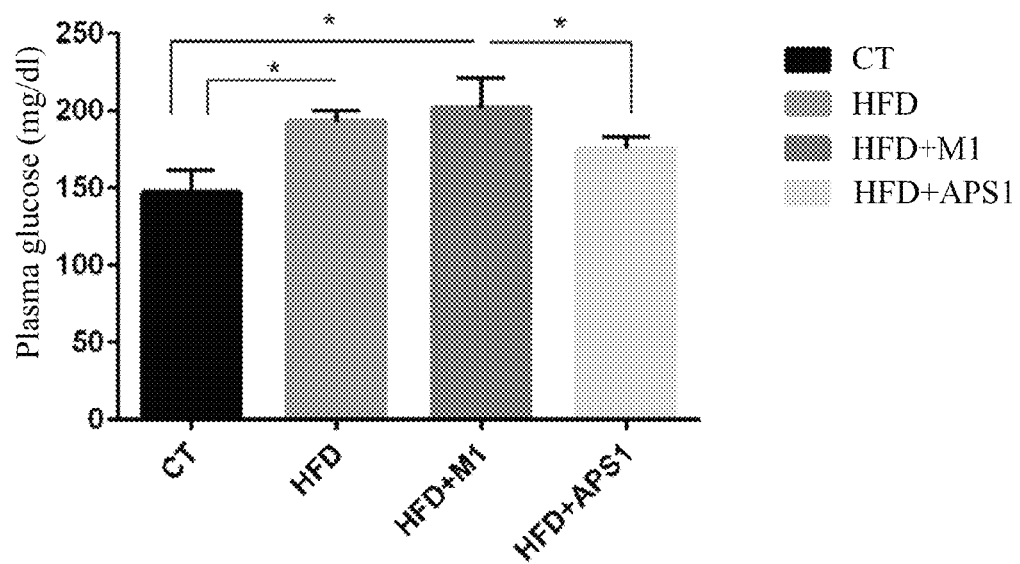

FIGS. 3A and 3B showed the changes of blood glucose and the area under curve of blood glucose ($AUG_{glucose}$) at the $4^{th}$ week, respectively. FIGS. 3C and 3D showed the changes of blood glucose and the area under curve of blood glucose ($AUG_{glucose}$) at the $8^{th}$ week, respectively. FIG. 3E showed the glucose level in blood at the $8^{th}$ week.

As shown in FIGS. 3A to 3E, high-fat diet resulted in the decreased glucose tolerance. It implied that, in comparison with the control group, the action time of insulin in the body was increased and the sign of hyperglycemia was induced in HFD group. While Lb. mali APS1 could effectively reduce the glucose level and $AUG_{glucose}$, thereby increasing the glucose tolerance, and alleviating the sign of hyperglycemia induced by high-fat diet. There was no significant difference in glucose level and $AUG_{glucose}$ between APS1 group and CT group.

Example 10: Metabolic Hormone Determination

The levels of metabolic hormones in blood were determined in this Example. After the obesity animal model was established in the same manner as Example 5, the levels of insulin and GLP-1 in blood were determined by MILLI-PLEX® ELISA analysis kit (EMD Millipore Corporation, Billerica, Mass., U.S.A.). All metabolic hormones were added dipeptidyl peptidase-4 inhibitor before the determination for inhibiting the target degradation.

Figure 3F:
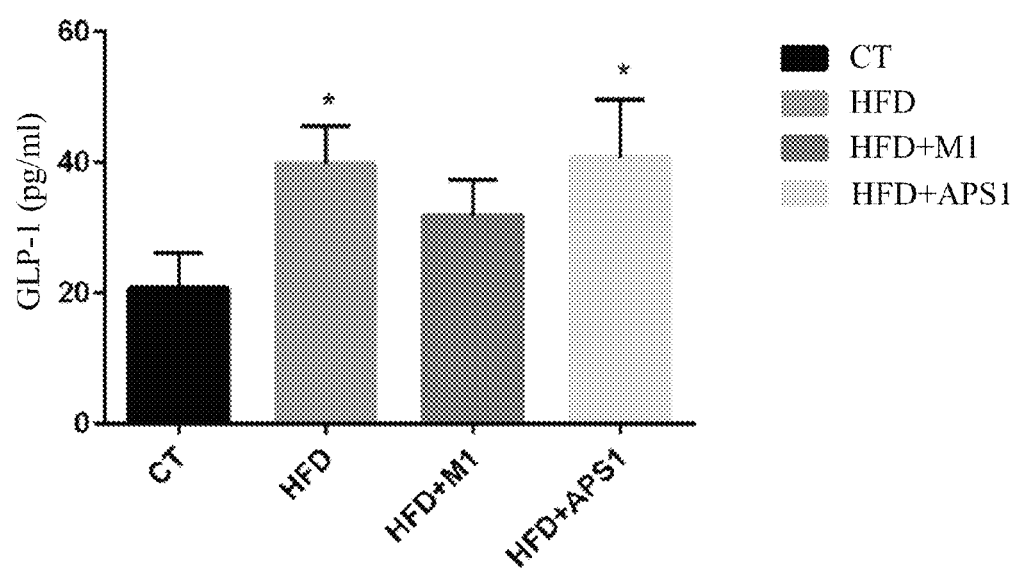
Figure 3G:
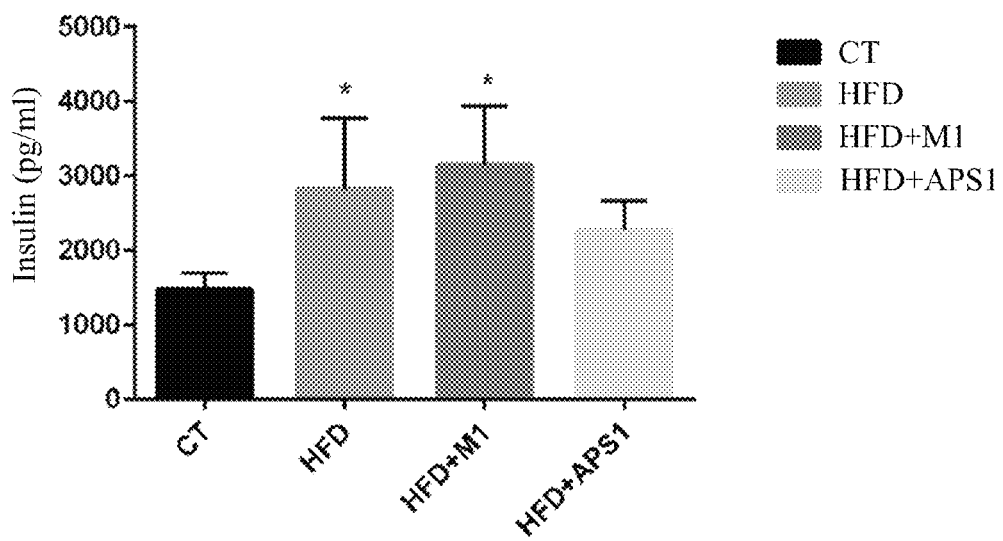

The results were shown in FIGS. 3F and 3G. Lb. mali APS1 could induce the GLP-1 production with higher level (40.08±8.83 pg/mL). The insulin level was higher in HFD group and M1 group (2823±95 pg/mL and 3146±793 pg/mL). These results were consistent with the weigh gain result. It implied that the level of blood glucose in obesity mice was higher in the long term, such that the insulin sensitivity is decreased. Also, since the impairments in production, storage, and secretion of insulin resulted in the increased compensatory secretion of insulin, the hyperglycemia was induced and the insulin level was high in body. These signs referred to the standard transitional stage of mid-term type 2 diabetes.

Figure 3H:
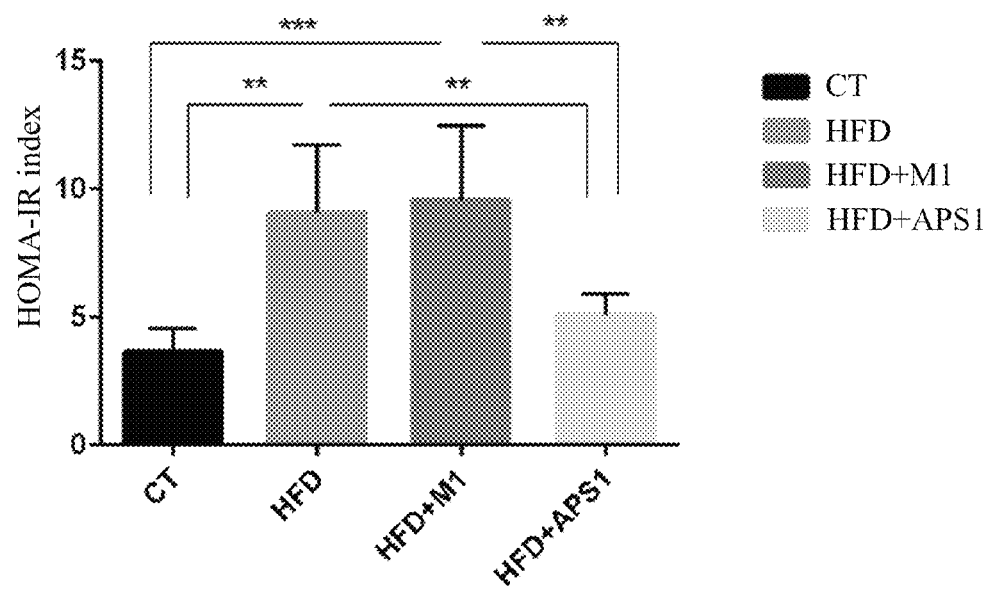
Figure 4A:
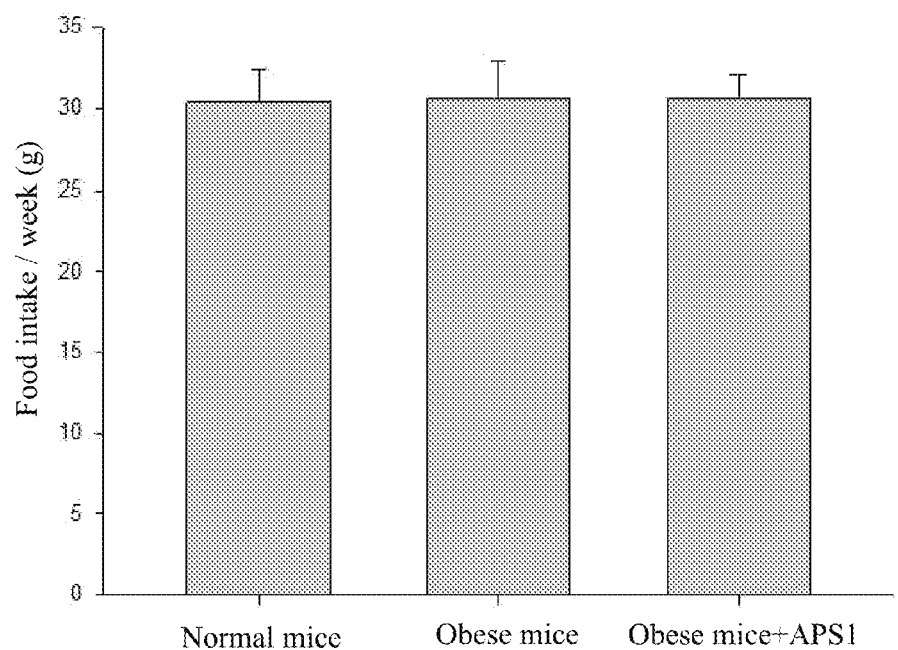
FIGS. 4A to 4D show the effect of *Lb. mali* APS1 on body weight loss in obese mice. After the mice were fed with high-fat diet for 8 weeks, the mice were fed with normal control diet with the addition of *Lb. mali* APS1 for 4 weeks.
Figure 4B:
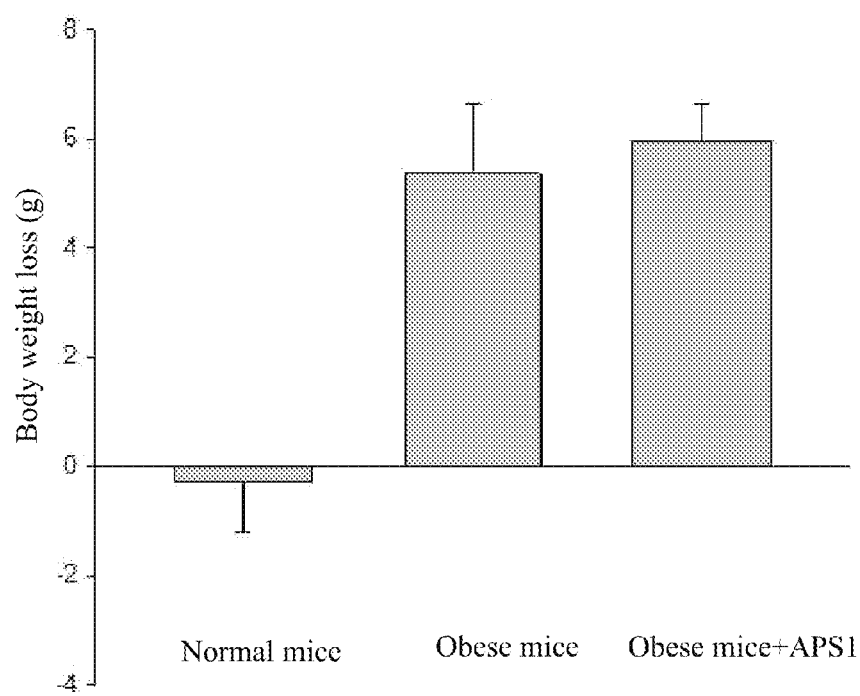
Figure 4C:
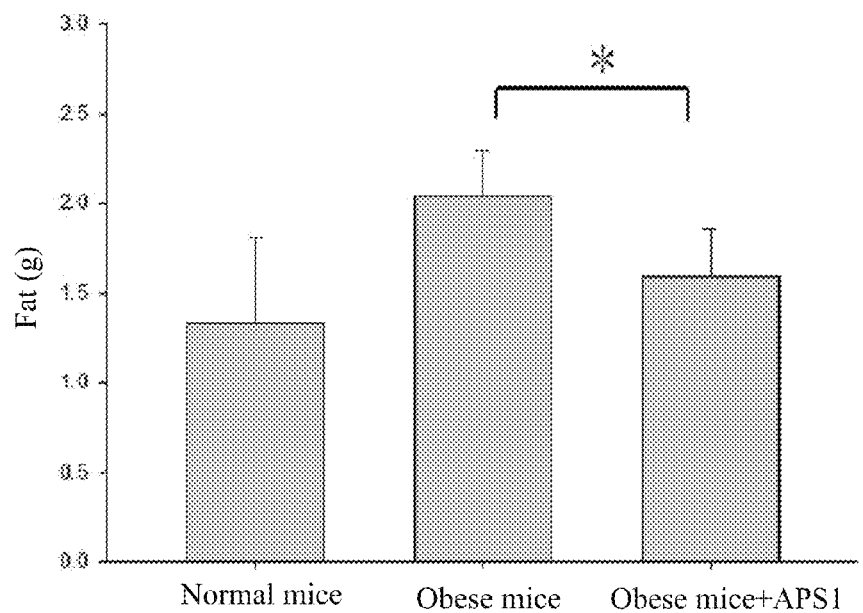
Figure 4D:
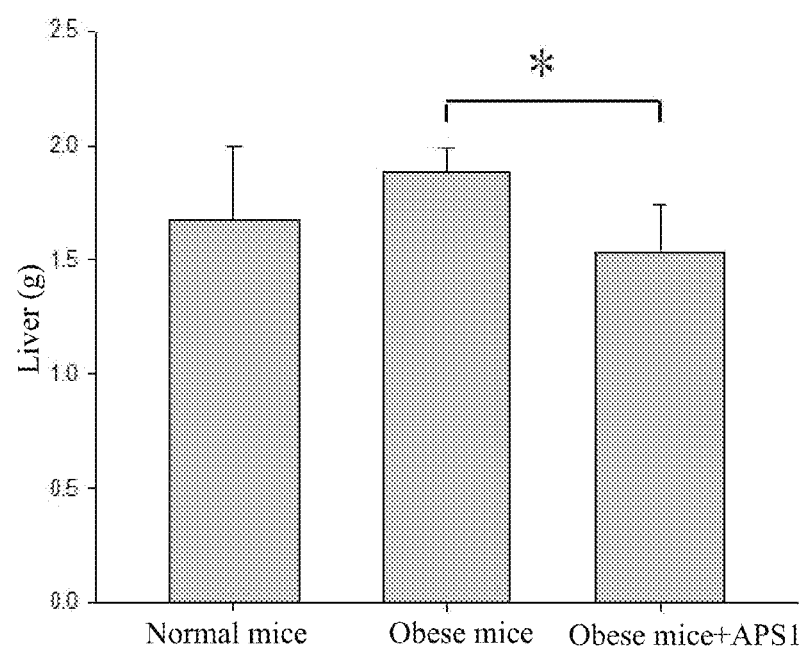

The results of the factors associated with blood glucose regulation were revaluated with insulin resistance index of Homeostatic Model Assessment-IR (HOMA-IR). As shown in FIG. 3H, the group fed with *Lb. mali* APS1 could significantly alleviate insulin resistance due to high-fat diet.

Example 11: Effects of *Lb. Mali* APS1 on Weight Loss in Mice Fed with Same Diets To mimic the weight control of a person on a diet, the weight loss in obesity mice was determined in this example. 30 six-week-old male C57BL/6jNarl (BioLASCO Taiwan Co., Ltd, Taipei, Taiwan) were housed in the same manner as Example 5. The mice were divided into 3 groups (10 per group): (1) normal mice group, fed with AIN-93-base refined diet; other groups were fed with high-fat diet modified from AIN-93-base diet, including (2) obese mice group, fed with high-fat diet for 8 weeks to induce obesity and then fed with the diet of normal mice group on week 9 with orally administrated with PBS daily; and (3) obese mice+APS1 group (probiotics group), fed with high-fat diet for 8 weeks to induce obesity and then fed with the diet of normal mice group on week 9 with orally administrated with $10^8$ CFU of *Lb. mali* APS1. After 1 month of feed change and oral administration, the body weight, body fat and liver weight of the mice were subject to comparison.

FIGS. 4A to 4D showed that the weights of mice in each group were decreased. Under the premise that the food intakes were not different (see FIG. 4A), the weight loss in obese mice+APS1 group was greater (see FIG. 4B). At the same time, the body fat was significantly decreased and the increased liver weight due to fat accumulation in obesity was alleviated in obese mice+APS1 group (see FIGS. 4C and 4D).

Example 12: Statistical Analysis

All experiments were repeated three times. The obtained data were drawn by Microsoft® Office Excel® 2010 (Microsoft Corp., Redmond, Wash., USA), and subject to analysis of variance (ANOVA) by SAS institute, ver.9.1 for Windows, Cary, N.C., USA. The significant difference between the means in each group was calculated by Duncan's new multiple range test.

From the above, in the obesity mice model, the results of weight change, body composition change, oral glucose tolerance analysis, plasma biochemical parameter analysis, and metabolic hormone determination demonstrated that *Lactobacillus mali* has an excellent ability to improve the metabolic syndrome and exhibits great effect on weight loss and inhibition of body fat production. Therefore, *Lactobacillus mali* is a probiotics having great potential, and it can be mixed with other probiotics or added into edible materials, or be a food, dietary supplement or feed supplement, and exhibits the effect on metabolic syndrome improvement. Besides, *Lactobacillus mali* can be mixed with a pharmaceutically acceptable carrier to prepare solution, suspension, emulsion, powder, tablet, pill, syrup, lozenge, troche, chewing gum, and capsule for general or pharmaceutical application.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claim.

What is claimed is:

1. A biologically pure *Lactobacillus mali* strain APS1, deposited under DSMZ Accession No. DSM 32117.

2. A composition, comprising the biologically pure *Lactobacillus mali* strain APS1 according to claim 1, and a carrier.

3. The composition according to claim 2, wherein said composition is a pharmaceutical composition, a dietary supplement or food.

4. The composition according to claim 2, wherein said composition is an oral formulation.

5. The composition according to claim 4, wherein the oral formulation is in a form selected from the group consisting of solution, suspension, emulsion, powder, tablet, pill, syrup, lozenge, troche, chewing gum, capsule and a combination thereof.

6. The composition according to claim 2, further comprising a bacterial strain selected from the group consisting of *Lactobacillus* sp., *Bifidobacterium* sp., *Streptococcus* sp., yeast, *Enterococcus* sp., *Bacillus* sp. and a combination thereof.

7. The composition according to claim 2, wherein the carrier is an edible material selected from the group consisting of water, milk, whey, fermented milk, yogurt, powdered milk, cheese, fruit juice, vegetable juice, soy milk, bean milk, fermented soy milk, sport drink, dessert, candy, Chinese herbal medicine, animal feed, corn starch, wheat starch, cassava starch, maltodextrin and a combination thereof.

8. A method for treating a metabolic syndrome in a subject, comprising orally administrating a composition comprising *Lactobacillus mali* APS1 deposited under DSMZ Accession No. DSM 32117, to the subject.

9. The method according to claim 8, wherein the metabolic syndrome is selected from the group consisting of obesity, diabetes, a complication of diabetes, hyperlipidemias, hyperglycemia, fatty liver, hyperuricemia, hypertension and a combination thereof.

10. The method according to claim 9, wherein the metabolic syndrome is obesity.

11. The method according to claim 10, wherein after the administration, a body weight of the subject is reduced and/or a weight gain in the subject is inhibited.

12. The method according to claim 10, wherein the obesity is resulted from body fat formation or increased content of visceral fat.

13. The method according to claim 9, wherein the metabolic syndrome is diabetes or a complication of diabetes.

14. The method according to claim 13, wherein the diabetes is resulted from a factor selected from the group consisting of insulin resistance, impaired glucose tolerance, hyperglycemia, hypertriglyceridemia, high total cholesterol, high ratio of LDL/HDL, low concentration of GLP-1 and a combination thereof.

15. The method according to claim 13, wherein the diabetes is type 2 diabetes.

16. The method according to claim 13, wherein the complication of diabetes is selected from the group consisting of retinopathy, nephropathy, neuropathy, cardiovascular disease and a combination thereof.

17. The method according to claim 13, wherein after the administration, an amount of one selected from the group consisting of glucose, total cholesterol and a combination thereof in the subject is reduced.

18. The method according to claim 13, wherein after the administration, an amount of incretin in the subject is increased.

19. The method according to claim 18, wherein the incretin is GLP-1.

* * * * *